United States Patent
Ji et al.

(10) Patent No.: US 10,407,028 B2
(45) Date of Patent: Sep. 10, 2019

(54) RAIN SENSOR AND WIPER DRIVING APPARATUS COMPRISING SAME

(71) Applicant: LG INNOTEK CO., LTD., Seoul (KR)

(72) Inventors: Chil Young Ji, Seoul (KR); Ki Chul Chang, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 0 days.

(21) Appl. No.: 15/556,924

(22) PCT Filed: Mar. 4, 2016

(86) PCT No.: PCT/KR2016/002197
§ 371 (c)(1),
(2) Date: Sep. 8, 2017

(87) PCT Pub. No.: WO2016/144054
PCT Pub. Date: Sep. 15, 2016

(65) Prior Publication Data
US 2018/0244244 A1    Aug. 30, 2018

(30) Foreign Application Priority Data

Mar. 12, 2015    (KR) ........................ 10-2015-0034390

(51) Int. Cl.
*B60S 1/08* (2006.01)
*G01N 27/22* (2006.01)
*G01N 27/06* (2006.01)

(52) U.S. Cl.
CPC .............. *B60S 1/0825* (2013.01); *B60S 1/08* (2013.01); *G01N 27/06* (2013.01); *G01N 27/223* (2013.01)

(58) Field of Classification Search
CPC . B60S 1/05; B60S 1/08; B60S 1/0825; G01N 27/06; G01N 27/223

(Continued)

(56) References Cited

U.S. PATENT DOCUMENTS

| | | | |
|---|---|---|---|
| 3,848,218 A | | 11/1974 | Wakabayashi et al. |
| 4,783,876 A | * | 11/1988 | Souma ................. B60S 1/0405 |
| | | | 15/250.02 |

(Continued)

FOREIGN PATENT DOCUMENTS

| | | |
|---|---|---|
| EP | 1318395 A2 | 6/2003 |
| EP | 2522554 A1 | 11/2012 |

(Continued)

OTHER PUBLICATIONS

International Search Report in International Application No. PCT/KR2016/002197, filed Jun. 29, 2016.

(Continued)

*Primary Examiner* — Gregory A Blankenship
(74) *Attorney, Agent, or Firm* — Saliwanchik, Lloyd & Eisenschenk

(57) ABSTRACT

A rain sensor according to an embodiment comprises: a substrate; a sensing electrode formed on a first surface of the substrate; a reaction layer formed on the first surface of the substrate and burying an upper surface of the substrate and the sensing electrode; a driving unit electrically connected to the sensing electrode formed on the first surface of the substrate and processing a sensing signal transmitted through the sensing electrode; and a protective layer formed surrounding the driving unit, wherein an impedance value according to a change of at least one of a force and a dielectric constant caused by presence of rainfall is changed, and the sensing electrode transmits the sensing signal with respect to a variation amount of the impedance value of the reaction layer to the driving unit.

8 Claims, 9 Drawing Sheets

(58) Field of Classification Search
USPC .................................................. 296/96.15
See application file for complete search history.

(56) References Cited

U.S. PATENT DOCUMENTS

| | | | |
|---|---|---|---|
| 6,806,722 | B2 | 10/2004 | Shon et al. |
| 2003/0159504 | A1 | 8/2003 | Barguirdjian et al. |
| 2007/0157720 | A1* | 7/2007 | Veerasamy ....... B32B 17/10036 73/170.17 |
| 2008/0018142 | A1 | 1/2008 | Yul |
| 2009/0039901 | A1* | 2/2009 | Delatte ................ B32B 17/10 324/664 |
| 2010/0255238 | A1* | 10/2010 | Derda .................. B32B 17/10 428/38 |
| 2011/0138567 | A1 | 6/2011 | Pearson |
| 2012/0286813 | A1 | 11/2012 | Murphy et al. |
| 2013/0024169 | A1* | 1/2013 | Veerasamy ....... B32B 17/10036 703/2 |
| 2018/0022320 | A1* | 1/2018 | Lee ..................... B60S 1/0825 324/663 |
| 2018/0045452 | A1 | 2/2018 | Ji et al. |
| 2018/0244244 | A1* | 8/2018 | Ji ........................... B60S 1/08 |

FOREIGN PATENT DOCUMENTS

| | | |
|---|---|---|
| EP | 3267186 A1 | 1/2018 |
| JP | 2010-096609 A | 4/2010 |
| JP | 2010-249531 A | 11/2010 |
| JP | 2011-232050 A | 11/2011 |
| KR | 10-0884123 B1 | 2/2009 |
| KR | 10-2009-0126754 A | 12/2009 |
| KR | 10-2014-0048501 A | 4/2014 |

OTHER PUBLICATIONS

Supplementary European Search Report dated Jan. 24, 2018 in European Application No. 16761941.0.

Nguyen, T.D. et al., Highly sensitive proximity and tactile sensor based on composite with dielectric elastomer and Carbon Microcoils, Proc. of SPIE, 2014, 9056:1-9, 2014 SPIE.

Chen, W. et al., A Capacitive Humidity Sensor Based on Multi-Wall Carbon Nanotubes (MWCNTs), *Sensors*, Aug. 24, 2009, 9:7431-7444, 2009 the authors.

* cited by examiner

RAIN SENSOR AND WIPER DRIVING APPARATUS COMPRISING SAME

CROSS-REFERENCE TO RELATED APPLICATIONS

This application is the U.S. national stage application of International Patent Application No. PCT/KR2016/002197, filed Mar. 4, 2016, which claims priority to Korean Application No. 10-2015-0034390, filed Mar. 12, 2015, the disclosures of each of which are incorporated herein by reference in their entirety.

TECHNICAL FIELD

An embodiment relates to a rain sensor, and more particularly, to a rain sensor capable of determining presence of rainfall and a rainfall amount based on impedance variation amount and driving a wiper based on a rainfall amount and a wiper driving apparatus comprising the same.

BACKGROUND ART

In general, a wiper is installed on the windshield of a vehicle in order to overcome a visibility obstacle caused by rainwater in a rainfall. These wipers control an intermittent speed thereof step by step depending on a dropping degree of rainwater. However, since a speed control system of the wiper is controlled by only a few steps, the wiper may not be operated at a speed a driver desires depending on an amount of rainwater.

In order to overcome this problem, a circuit board on which a light source and a sensor which is a light receiving element are mounted is inclined with respect to a windshield surface, so that a rain sensing efficiency can be increased by receiving only an optical signal reflected from raindrops themselves while minimizing an influence of light reflected from the windshield surface. That is, light directly reflected from the windshield goes outside a light receiving range of the light receiving element and is reflected on the windshield to minimize an amount of light received by the light receiving element. On the other hand, since only the amount of light reflected by the raindrops is received by the light receiving element, the circuit board having the light source and the light receiving element is disposed at an angle to the windshield surface so as to detect only an irregular reflection signal from the raindrops.

However, even in the case of a product in which the light source and the light receiving element are arranged with the circuit board inclined with respect to the windshield surface of the vehicle, the light emitted from the light source may be directly absorbed by the light receiving element, and thus the rain sensing efficiency is somewhat incomplete and insufficient. That is, the light emitted from the light source spreads over a range of angles, and even if the light source and the light receiving element are arranged so as to be inclined with respect to the windshield surface, a part of the light is directly emitted toward the light receiving element other than the light coming out of the windshield. Thus, there is a problem of somewhat lowering the raindrop detection efficiency due to interference light absorbed by the light receiving element from the light source.

Even in the case of designing to minimize ambient interference light due to headlight of the around traveling vehicles as described above, interference light which may not inevitably be blocked is generated. A light sensing rain sensor itself is a very sensitive sensor product, so that a small amount of ambient light that may not be blocked inevitably affects the sensor, and thus it can not help but have a limit to have a highly accurate rain sensing effect. In addition, in order to realize a structure for minimizing the influence of the ambient light, it has no choice but to have a somewhat complicated structure, thereby inevitably having a limitation such as a somewhat inefficiency in productivity and a somewhat higher product cost.

DISCLOSURE

Technical Problem

In an embodiment according to the present invention, there is provided a rain sensor which detects a change in impedance caused by raindrops falling on a windshield of a vehicle and determines presence of rainfall and a rainfall amount, and a wiper driving apparatus including the same.

In addition, in an embodiment, there is provided a rain sensor which may determine presence of rainfall and a rainfall amount using a carbon micro-coil device and accordingly capable of controlling a driving condition of the wiper and a driving speed of the wiper, and a wiper driving apparatus including the same.

The technical problems to be solved in the proposed embodiments are not limited to the technical problems mentioned above, and other technical problems not mentioned may be clearly understood by those skilled in the technical field to which the embodiments proposed from the description below belong.

Technical Solution

A rain sensor according to an embodiment comprises: a substrate; a sensing electrode formed on a first surface of the substrate; a reaction layer formed on the first surface of the substrate and burying an upper surface of the substrate and the sensing electrode; a driving unit electrically connected to the sensing electrode formed on the first surface of the substrate and processing a sensing signal transmitted through the sensing electrode; and a protective layer formed surrounding the driving unit, wherein an impedance value according to a change of at least one of a force and a dielectric constant caused by presence of rainfall is changed and the sensing electrode transmits the sensing signal with respect to a variation amount of the impedance value of the reaction layer to the driving unit.

In addition, the reaction layer includes a carbon micro-coil material.

Further, the reaction layer includes a carbon micro-coil material, a resin, and a dispersant.

Furthermore, the reaction layer is disposed on the substrate on which the sensing electrode having a predetermined thickness is formed.

In addition, the sensing electrodes are formed in plural number, wherein each of the plurality of sensing electrodes includes a first electrode part disposed in an edge region of the substrate and a second electrode part extending in a longitudinal direction of the substrate from one end of the first electrode part, and the internal angle between the first electrode and the second electrode parts is an obtuse angle.

In addition, the rain sensor further includes a via formed through the substrate, wherein one end of the via is connected to the sensing electrode, and the other end is connected to the driving unit.

Further, the reaction layer causes a change in an imaginary part of a positive of impedance due to a force applied by the occurrence of the rainfall and a change in a negative imaginary part of impedance due to a change in a dielectric constant caused by an object existing on the second surface.

Further, a wiper driving apparatus according to an embodiment includes: a windshield; a sensor unit attached to a first surface of the windshield and having impedance value changed by an object contacting a second surface of the windshield; and a control unit for receiving a sensing signal corresponding to a variation amount of the impedance value through the sensor unit, determining presence of rainfall based on the received sensing signal, and driving a wiper depending on the determined presence of rainfall.

In addition, the sensor unit includes a substrate, a sensing electrode formed on a first surface of the substrate, a reaction layer formed on the first surface of the substrate and burying an upper surface of the substrate and the sensing electrode, a driving unit electrically connected to the sensing electrode formed on the first surface of the substrate and processing a sensing signal transmitted through the sensing electrode, and a protective layer formed surrounding the driving unit, wherein an impedance value of the reaction layer is changed by the contact object, and the sensing electrode transmits the sensing signal with respect to the impedance value of the reaction layer to the driving unit.

In addition, the reaction layer includes a carbon micro-coil material.

Further, the reaction layer includes a carbon micro-coil material, a resin, and a dispersant.

Furthermore, the reaction layer is disposed on the substrate on which the sensing electrode having a predetermined thickness is formed.

In addition, the sensing electrodes are formed in plural number, wherein each of the plurality of sensing electrodes includes a first electrode part disposed in an edge region of the substrate and a second electrode part extending in a longitudinal direction of the substrate from one end of the first electrode part, and the internal angle between the first electrode and the second electrode parts is an obtuse angle.

In addition, the sensor unit further includes a via formed through the substrate, wherein one end of the via is connected to the sensing electrode, and the other end is connected to the driving unit.

Further, the sensor unit detects presence of rainfall and a rainfall amount based on a change of a positive imaginary part of impedance due to a force applied to the second surface of the windshield by the contact object and a change of a negative imaginary part of impedance due to a change of a dielectric constant by an object existing on the second surface.

In addition, the sensor unit further includes an adhesive member disposed between the first surface of the windshield and the rain sensor unit.

Further, the control unit sets whether the wiper is driven or not and the driving speed based on a variation amount of the impedance value.

Advantageous Effects

According to an embodiment, when a rainfall occurs, by instantly reacting to the rainfall, a wiper is driven under driving conditions depending on an amount of rainfall, thereby improving convenience of a driver in case of rainy weather.

Further, according to an embodiment, presence of rainfall and a rainfall amount are determined using the carbon micro-coil device, thereby providing a rain sensor having differentiated characteristics such as response characteristics, precision, accuracy, power consumption, miniaturization, and the like in comparison with a conventional optical system.

MODES OF THE INVENTION

Figure 1:
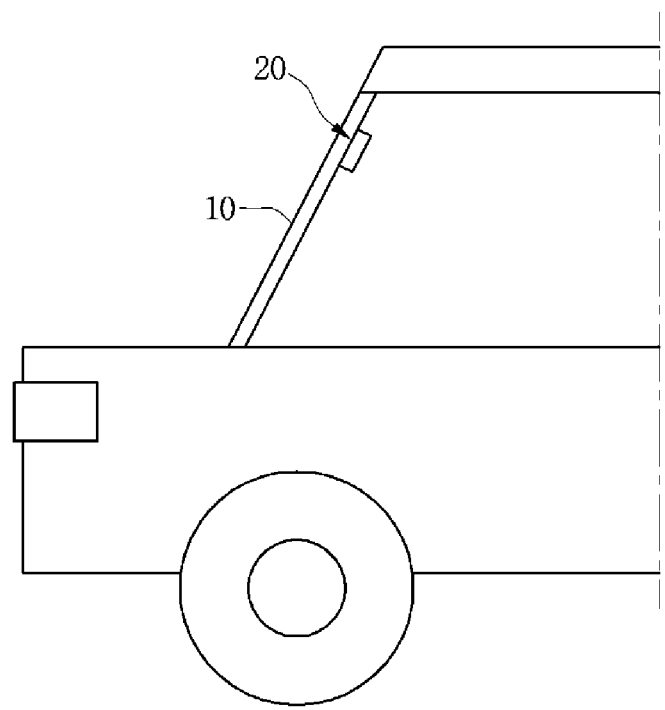
FIG. 1 is a side view illustrating a state where a rain sensor is mounted on a windshield of a vehicle according to an embodiment of the present invention.

Advantages, features, and methods of achieving the same of the present disclosure will become clear upon referring to embodiments described below in detail with reference to the accompanying drawings. However, the present disclosure is not limited to the embodiments disclosed below and may be implemented in various other forms. The embodiments are merely provided to make the disclosure of the present disclosure complete and completely inform one of ordinary skill in the art to which the present disclosure pertains of the scope of the present disclosure. The present disclosure is defined only by the scope of the claims below. Like reference numerals refer to like elements throughout.

In describing embodiments of the present disclosure, when detailed description of a known function or configuration is deemed to unnecessarily blur the gist of the present disclosure, the detailed description will be omitted. Terms described below are terms defined in consideration of functions in the embodiments of the present disclosure and may vary depending on the intention of a user or operator or a practice. Therefore, such terms should be defined on the basis of the entire contents disclosed herein.

Combinations of blocks and steps of flowcharts in the accompanying drawings can be performed by computer program instructions. Such computer program instructions can be embedded in a processor of a general-purpose computer, a special-purpose computer, or other programmable data processing equipment. Therefore, the instructions performed by the processor of a computer or other programmable data processing equipment generate means for performing functions described in each of the blocks or each of the steps in the flowcharts in the drawings. Because the computer program instructions can also be saved in a computer-usable or computer-readable memory capable of supporting a computer or other programmable data processing equipment to implement a function in a specific way, the instructions stored in the computer-usable or computer-readable memory can also produce a manufacturing item which incorporates an instruction means performing a function described in each of the blocks or each of the steps of the flowcharts in the drawings. Because the computer program instructions can also be embedded in a computer or other programmable data processing equipment, the instructions performed in a computer or other programmable data processing equipment by a process executed in a computer being generated by a series of operation steps being performed in the computer or other programmable data processing equipment can also provide steps for executing functions described in each of the blocks and each of the steps of the flowcharts in the drawings.

Each of the blocks or each of the steps may represent a module, a segment, or a part of a code including one or more executable instructions for executing a specified logical function(s). Also, it should be noted that functions mentioned in the blocks or steps can also be performed in a different order in a few alternative embodiments. For example, two blocks or steps which are consecutively illustrated can substantially be performed simultaneously, or the blocks or steps can also be performed in a reverse order sometimes according to corresponding functions.

Figure 2:
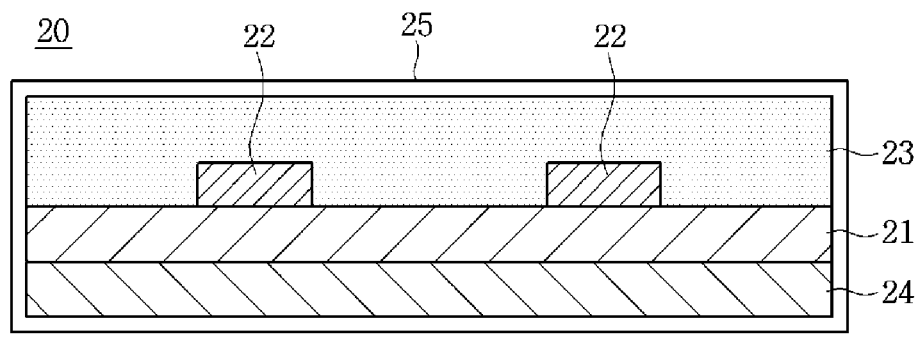
FIG. 2 is a sectional view illustrating the detailed structure of the rain sensor shown in FIG. 1.
Figure 3A:
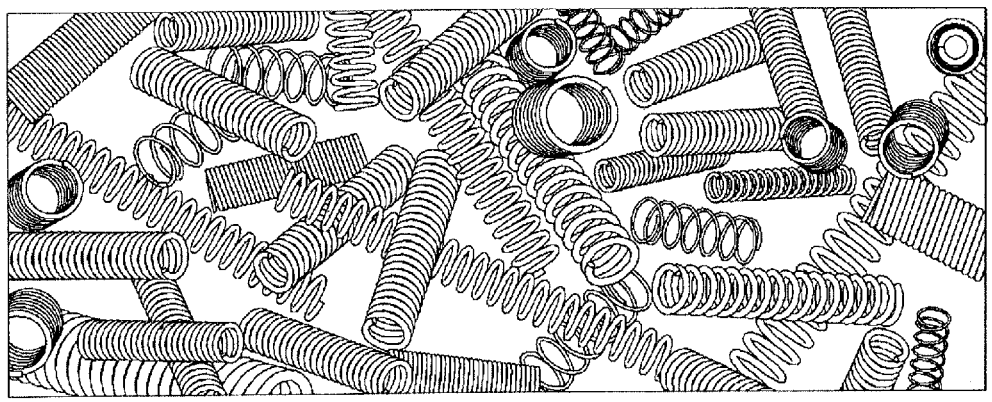
FIGS. 3a and 3b are views illustrating a reaction layer shown in FIG. 2.
Figure 3B:
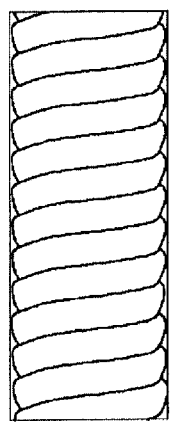
Figure 4:
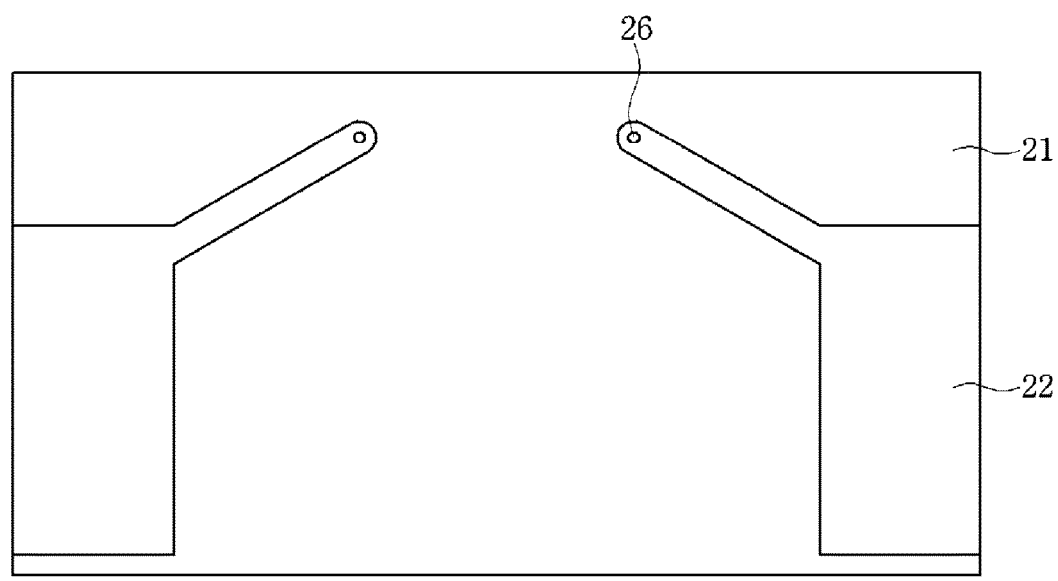
FIG. 4 is a plan view of a sensing electrode shown in FIG. 2.

FIG. 1 is a side view illustrating a state where a rain sensor is mounted on a windshield of a vehicle according to an embodiment of the present invention, FIG. 2 is a sectional view illustrating the detailed structure of the rain sensor shown in FIG. 1, FIGS. 3a and 3b are views illustrating a reaction layer shown in FIG. 2, and FIG. 4 is a plan view of a sensing electrode shown in FIG. 2.

Referring to FIGS. 1 to 4, a rain sensor 20 is mounted on a windshield 10 of a vehicle.

The rain sensor 20 is installed so as to face the windshield 10 of the vehicle and detects a change in impedance depending on whether there are raindrops falling on the windshield 10 or an amount of the raindrops.

The rain sensor 20 forms a sensing region at a predetermined position of the windshield 10 of the vehicle and senses information depending on the state of raindrops generated in the sensing region.

Referring to FIG. 2, the rain sensor 20 includes a substrate 21, a sensing electrode 22, a reaction layer 23, a driving unit 24, and a protective layer 25.

The rain sensor 20 as described above, detects a change in impedance depending on a presence or absence of raindrops falling on the windshield 10 in a certain area inside the windshield 10 of the vehicle, and provides information for driving wipers.

The substrate 21 is a base substrate on which the sensing electrode 22, the reaction layer 23, and the driving unit 24 are mounted.

The sensing electrode 22 is formed on the substrate 21. The sensing electrode 22 is formed on an upper surface of the substrate 21 while being buried by the reaction layer 23.

The sensing electrode 22 may be formed in plural number. The sensing electrode 22 senses a change in impedance as a reaction of the reaction layer 23 occurs due to a material formed on a surface of the reaction layer 23.

Preferably, the sensing electrode 22 may include a first sensing electrode having a positive polarity and a second sensing electrode having a negative polarity.

The reaction layer 23 is formed on the substrate 21 and is formed by burying the upper surface of the substrate 21 and the sensing electrode 22.

Preferably, the reaction layer 23 is formed on the substrate 21 on which the sensing electrode 22 having a predetermined thickness is formed.

The reaction layer 23 is formed of a conductive material and has a property in which the impedance varies depending on a change in a force or a dielectric constant generated by an external material.

Preferably, the reaction layer 23 is a carbon micro-coil (CMC) having a spring shape. That is, the reaction layer 23 is formed by depositing at least one of hydrocarbons such as acetylene, methane, propane, and benzene on the substrate 21 by a chemical vapor deposition (CVD) process.

In addition, otherwise, the reaction layer 23 may be formed using a metal catalyst on the basis of nickel or nickel-iron.

As described above, the CMC, as shown in FIGS. 3a and 3b may have a shape which is not straight, but is curled like a pig tail and is amorphous carbon fiber with a unique structure a fiber material may not have. Further, the CMC has a superelasticity which extends to a length, which is ten times or more that of an original coil.

FIG. 3a illustrates a coil formed in the reaction layer 23, and FIG. 3b is a detailed view of the coil.

Morphology of the reaction layer 23 has a 3D-helical/spiral structure, and the crystal structure is amorphous.

In other words, the reaction layer 23 as described above is formed by growing carbon fibers into a coil shape, and accordingly, the reaction layer 23 has a cross-sectional structure in which carbon fibers are grown in a coil shape.

That is, in the reaction layer 23, a change in impedance of the reaction layer 23 occurs due to a force applied by a contact of a specific material to the surface of the windshield 10 to which the rain sensor 20 is attached or a dielectric constant of the specific material.

Furthermore, the sensing electrode 22 senses a change in impedance of the reaction layer 23, thereby transmitting a sensing signal corresponding to the change in impedance to the driving unit 24.

The driving unit 24 is formed on a lower surface of the substrate 21. Accordingly, the driving unit 24 detects presence of rainfall and a rainfall amount depending on a sensing signal transmitted through the sensing electrode 22, and generates a control signal for controlling an operation of the wiper depending on the detected presence of rainfall and rainfall amount.

That is, in general, REAL TERM of impedance is resistance, POSITIVE IMAGINARY TERM is inductance, and NEGATIVE IMAGINARY TERM is capacitance, and the impedance consists of a summation of the resistance, inductance and capacitance.

Therefore, the rain sensor 20, like a general resistor, an inductor, and a capacitor, also needs a pair of sensing electrodes 22 so as to detect a change in impedance generated in the reaction layer 23. The sensing electrode 22 functions to connect the reaction layer 23 and the driving unit 24 while optimizing the sensing characteristics of the reaction layer 23.

Here, when a specific force is applied to the surface of the windshield 10 or a material having a specific dielectric constant is contacted, a capacitance of the reaction layer 23 is increased. Accordingly, a resistance value and an inductance value are decreased as opposed to the capacitance.

At this point, the sensed impedance value is a summation of the resistance value, the inductance value, and the capacitance value, and the impedance value is linearly decreased depending on a degree of the force or dielectric constant applied to the surface.

At this point, the sensing electrode 22 has a structure as shown in FIG. 4 and is formed on the substrate 21.

The sensing electrode 22 includes a first electrode part formed on an edge region of the substrate 21 and a second electrode part extending from one end of the first electrode part to a central region of the substrate and having a predetermined inclination angle with respect to the one end of the first electrode part.

That is, a state of change in impedance generated in the reaction layer 23 varies depending on the shape of the sensing electrode 22.

Accordingly, in the present invention, in order to optimally adjust the state of change in impedance of the reaction layer 23, as described above, the sensing electrode 22 including the first electrode part and the second electrode part is formed on the substrate 21.

Meanwhile, a via 26 is formed at a lower portion of one end of the second electrode part.

The via 26 is formed by burying a through hole passing through the upper and lower surfaces of the substrate 21 with a metal material.

One end of the via 26 is connected to the sensing electrode 22 by passing through the substrate 21, and the other end of the via 26 is connected to the driving unit 24 attached to the lower surface of the substrate 21.

Meanwhile, the driving unit 24 is provided with an analog front end (AFE) and is connected to the sensing electrode 22 through the via 26.

At this point, the AFE performs a differential amplification function, and there is a difference in the state of change of the impedance according to the generation of the rainfall depending on whether the differential amplification is positive or negative.

Accordingly, the driving unit 24 senses a state of change of the impedance value based on a reference value according to the differential amplification state, and when a degree of the state of change deviates from a critical value, the wiper is driven to remove raindrops.

Hereinafter, the driving step of the wiper will be described in more detail.

That is, when raindrops are falling, the raindrops apply a certain force on the windshield 10 or cause a change in the dielectric constant.

In addition, impedance variation occurs in the reaction layer 23 depending on the change in the applied force or the dielectric constant.

At this point, the variation amount of the impedance may correspond to the presence of rainfall and rainfall amount. That is, the force or the dielectric constant applied to the reaction layer 23 is increased in proportion to the rainfall amount, and the impedance variation amount is decreased in inverse proportion to the increase of the dielectric constant or the force.

As described above, when the rainfall occurs, a change in impedance of the reaction layer 23 occurs, and an amplitude change with respect to an internal clock of the driving unit 24 occurs depending on the impedance variation.

Further, a differential signal depending on the differential amplification of the AFE of the driving unit 24 is output depending on the amplitude change of the internal clock.

Then, when the differential signal is output, the output differential signal is converted into a digital signal and transmitted to a main control unit (to be described later) of the vehicle.

The main control unit (not shown) detects the presence of rainfall and the rainfall amount based on an impedance variation amount depending on the digital signal transmitted. When the rainfall occurs and the rainfall amount exceeds a critical point, the wiper is operated to remove raindrops.

Figure 5:
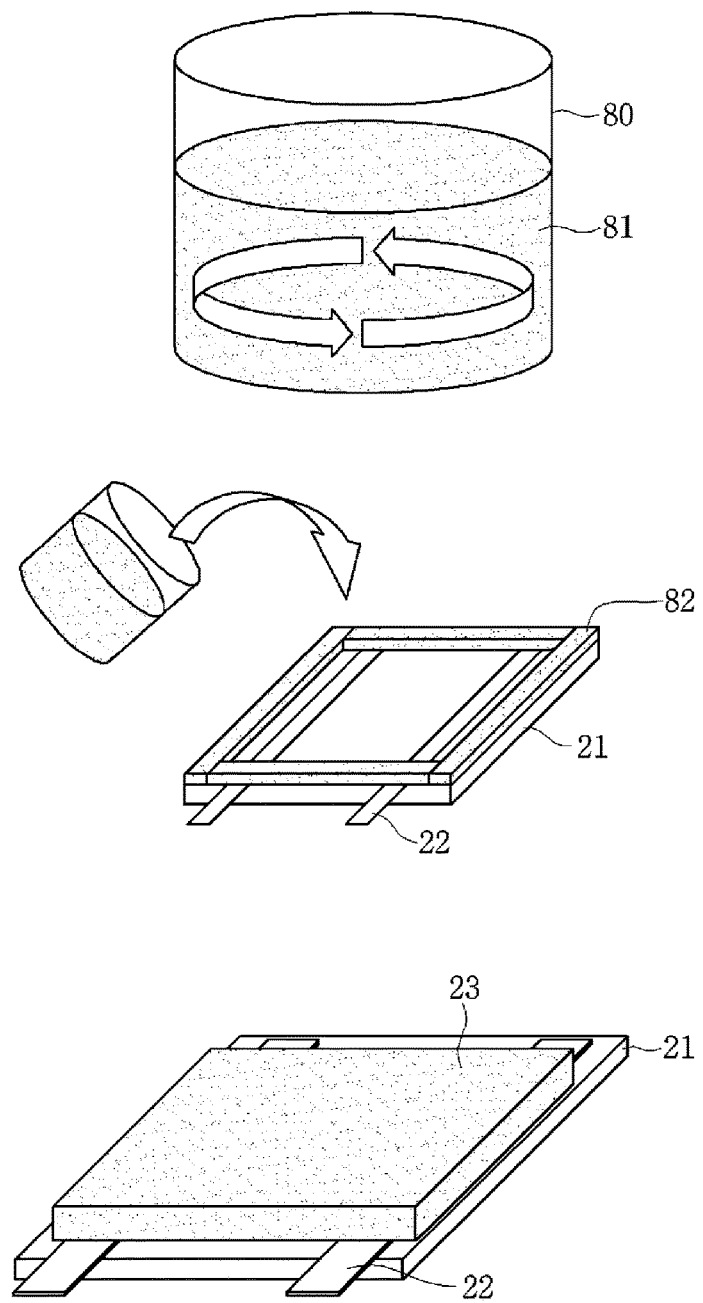
FIG. 5 is a view for explaining a method of manufacturing a rain sensor 20 shown in FIG. 2.

FIG. 5 is a view for explaining a method of manufacturing the rain sensor 20 shown in FIG. 2.

Referring to FIG. 5, a solution 81 for forming the reaction layer 23 is first prepared in a plating tank 80.

The solution 81 may be made of a carbon micro-coil material (CMC material). At this point, the solution 81 may include only the carbon micro-coil material, and otherwise, resin and dispersant may be further added.

As described above, in a first step, a carbon micro-coil material and a resin are added and mixed in the plating tank 80, and thereafter, the dispersant is further added and dispersed. The dispersant is for dispersing the solution evenly on the substrate 21 later.

Then, a substrate 21 is prepared and a sensing electrode 22 is formed on the prepared substrate 21.

The sensing electrodes 22 are formed in plural number, and have a planar structure as shown in FIG. 4.

Then, a frame 82 is formed in an edge region of the substrate 21. The frame 82 exposes a central region of the substrate 21 and is formed on the substrate 21 while covering the edge region of the substrate 21.

Then, the prepared solution 81 is injected into the frame 82 of the substrate 21.

In addition, a reaction layer 23 is formed on the basis of the injected solution 81 through a curing process.

At this point, the curing process may be performed at a temperature of 120° C. for 30 minutes.

Hereinafter, the driving principle of the rain sensor 20 will be described in more detail.

As described above, the sensing electrode 22 is embedded in the reaction layer 23 configured with a carbon micro-coil (CMC). The sensing electrode 22 is connected to the driving unit 24 mounted on the lower surface of the substrate 21 through the via 26.

At this point, the reaction layer 23 itself may determine the presence of rainfall and the rainfall amount depending on an impedance variation amount, and the measurement sensitivity varies depending on a shape of the sensing electrode 22. Accordingly, in an embodiment, the sensing electrode 22 having the planar shape as described above is formed.

Therefore, in the embodiment, optimization of various factors such as composition of adjusting carbon micro-coil content ratio, optimized electrode shape, and mounting position of the driving unit 24, and the like is important.

In addition, as described above, the impedance is composed of a real part (real) and an imaginary part (reactance), and the imaginary part is composed of a positive imaginary part (inductive) and a negative imaginary part (capacitive). At this point, the rain sensor 20 including the carbon micro-coil is measured using two characteristic changes of the positive imaginary part (inductive) and negative imaginary part (capacitive).

That is, when the rain comes, a force applied to the windshield 10 of the vehicle changes depending on an amount of rain, and an amount of water (raindrops) present on the windshield 10 is also changed.

At that point, a carbon micro-coil (CMC), as the name describes, is composed of a very fine collection of coils, and is also an electric conductor having a dielectric constant.

At this point, the force is measured by an inductive ingredient change, that is, by a characteristic change of a carbon micro-coil, and an amount of water present on the windshield 10 is measured by a capacitive change due to a change in a dielectric constant.

That is, each layer constituting the rain sensor 20 functions as a dielectric having a specific dielectric constant, and in the case of rainfall as described above, in an aspect of the electrode, a water-like dielectric is newly present, and leads to a capacitive change.

At this point, a real part (real) may be adjusted depending on an area of the reaction layer 23, and in the case of rainfall, as described above, the impedance value changes due to changes in inductive and capacitive values.

Therefore, in an embodiment, a change of a impedance value depending on a variation of an inductive and capacitive value of the rain sensor 20 as described above is detected to determine presence of rainfall and a rainfall amount.

Meanwhile, the rain sensor 20 as described above forms an adhesive member (not shown) such as silicone on the inside of the windshield 10 and is mounted on a specific inner area of the windshield 10 by the adhesive member.

At this point, the rain sensor 20 detects a change in impedance in consideration of a dielectric constant of the adhesive member.

Figure 6:
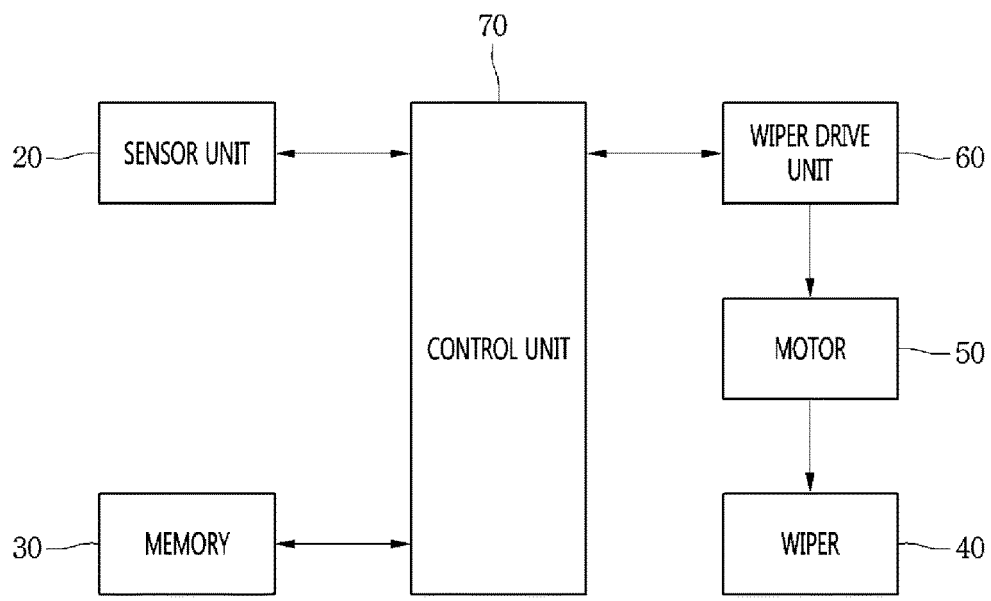
FIG. 6 is a view illustrating a wiper driving apparatus according to the embodiment.

FIG. 6 is a view illustrating a wiper driving apparatus according to an embodiment.

Referring to FIG. 6, the wiper driving apparatus includes a sensor unit 20, a memory 30, a wiper 40, a motor 50, a wiper drive unit 60, and a control unit 70.

The sensor unit 20 refers to the rain sensor, detects a change in impedance that is generated depending on the presence of rainfall, and transmits sensing information on a corresponding impedance variation amount to the control unit 70.

The memory 30 stores information for controlling various components of a vehicle.

In particular, the memory 30 includes driving condition information of a wiper depending on an amount of a change in impedance sensed through the sensor unit 20.

The driving condition information may include whether the wiper is driven or not and information on the driving speed of the wiper.

The wiper 40 is mounted on the outside of the windshield 10 of the vehicle and removes water such as raindrops present on the windshield 10.

The motor 50 drives the wiper 40 depending on predetermined conditions.

The wiper drive unit 60 provides the motor 50 with condition information for driving the wiper 40.

The condition information may be information of driving power to be supplied to the wiper 40 through the motor 50.

The control unit 70 receives sensing information on an amount of change in impedance obtained through the sensor unit 20.

In addition, the control unit 70 sets driving conditions for driving the wiper 40 based on the received sensing information.

Figure 7:
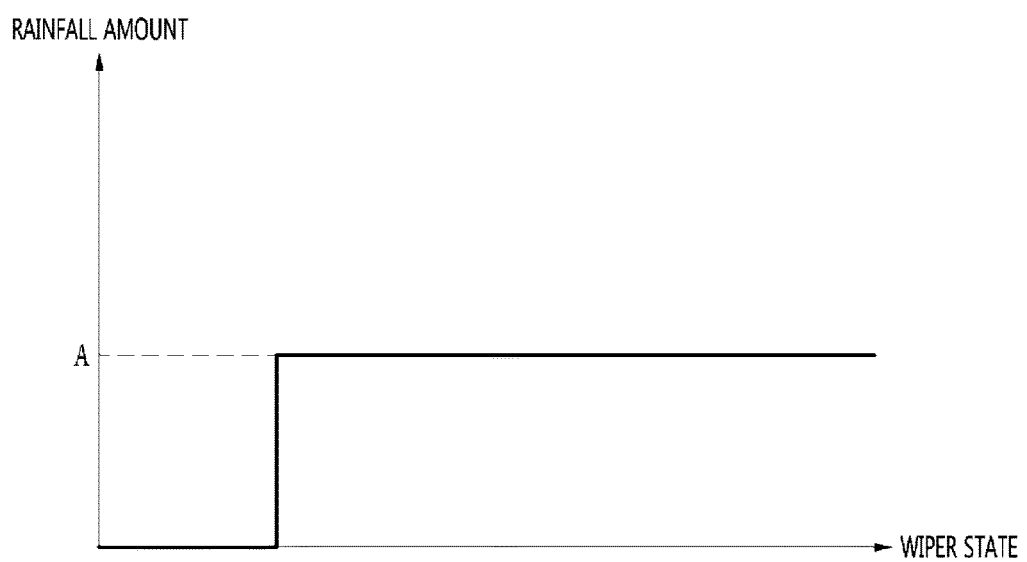
FIGS. 7 and 8 are views for explaining driving conditions of a wiper according to the embodiment of the present invention.
Figure 8:
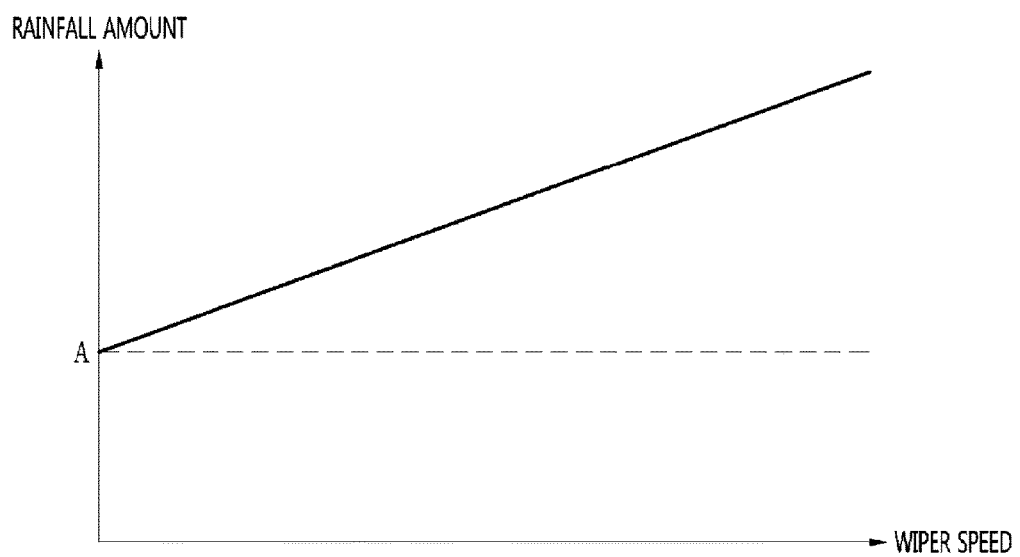

FIGS. 7 and 8 are views for explaining driving conditions of a wiper according to an embodiment of the present invention.

Referring to FIG. 7, the control unit 70 determines whether the sensing information corresponding to a critical point A has been received or not, as described above.

In other words, the control unit 70 determines whether an impedance variation amount due to the rainfall exceeds the critical point or not. In addition, the control unit 70 starts the operation of the wiper 40 when the impedance variation amount exceeds the critical point.

At this point, referring to FIG. 8, the control unit 70 determines a driving speed of the wiper 40 depending on a magnitude of the impedance variation amount.

That is, the control unit 70 increases a driving speed of the wiper 40 in proportion to an amount of change in impedance.

According to an embodiment, when a rainfall occurs, by instantly reacting to the rainfall, a wiper is driven under driving conditions depending on an amount of rainfall, thereby improving convenience of a driver in case of rainy weather.

Further, according to an embodiment, presence of rainfall and a rainfall amount are determined using a carbon microcoil device, thereby providing a rain sensor having differentiated characteristics such as response characteristics, precision, accuracy, power consumption, miniaturization, and the like in comparison with a conventional optical system.

Figure 9:
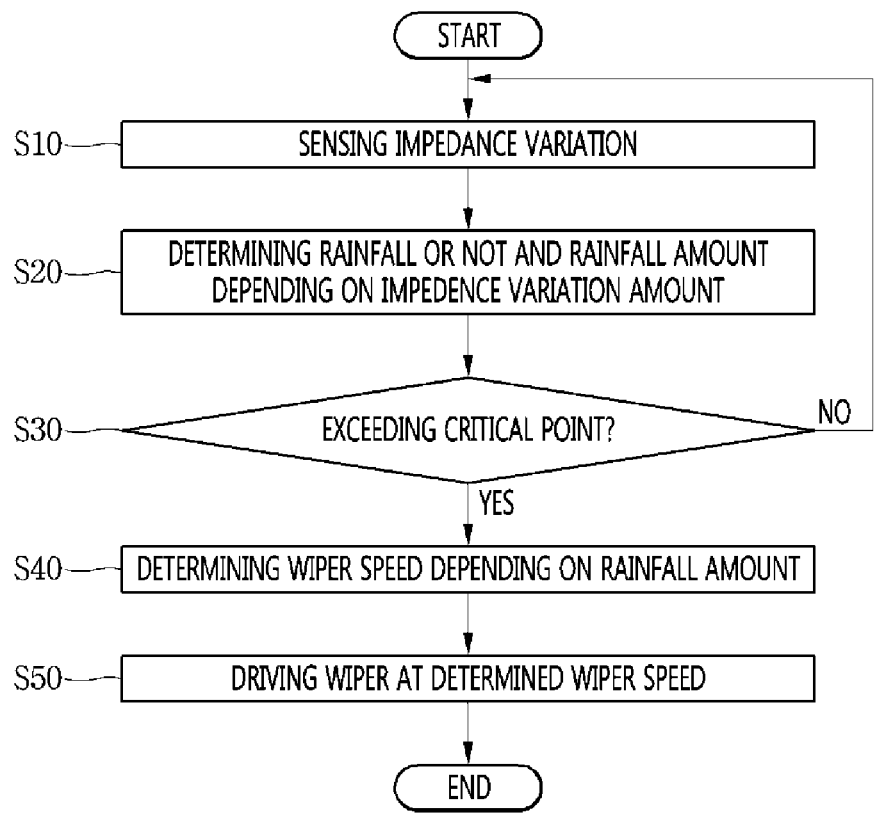
FIG. 9 is a flowchart illustrating a method of operating a rain sensor according to the embodiment of the present invention.

FIG. 9 is a flowchart illustrating a method of operating a rain sensor according to the embodiment of the present invention.

Referring to FIG. 9, the rain sensor 20 senses a change in impedance depending on whether rainfall occurs or not in the windshield 10 of the vehicle in step S10.

The rain sensor 20 transmits sensing information on the sensed impedance variation to the control unit 70.

The control unit 70 receives sensing information indicating the impedance variation, and determines presence of rainfall and a rainfall amount depending on an amount of impedance variation based on the sensed information in step S20.

Then, when the rainfall has occurred, the control unit 70 determines whether the rainfall amount exceeds a critical point or not in step S30. Whether or not the critical point is exceeded may be determined by whether the impedance variation amount exceeds the critical point.

In addition, when the rainfall amount exceeds the critical point, the control unit 70 determines a driving speed of the wiper 40 to be driven depending on the rainfall amount in step S40.

Then, the control unit 70 drives the wiper 40 at the determined driving speed in step S50.

Further, although preferred embodiments of the present disclosure have been shown and described, the present disclosure is not limited to the particular embodiments mentioned above. The embodiments may be modified in various ways by those of ordinary skill in the art to which the present disclosure pertains without departing from the gist of the present disclosure which is claimed in the claims below, and the modified embodiments should not be understood as being separate from the technical spirit or prospect of the present disclosure.

The invention claimed is:

1. A wiper driving apparatus comprising:
a windshield;
a sensor unit attached to a first surface of the windshield and having impedance value changed by an object contacting a second surface of the windshield; and
a control unit that receives sensing information corresponding to a variation amount of the impedance value through the sensor unit, determining presence of rainfall based on the sensing information, and driving a wiper depending on the determined presence of rainfall;
wherein the sensor unit comprises:
a substrate, a sensing electrode formed on a first surface of the substrate, a reaction layer formed on the first surface of the substrate to bury an upper surface of the substrate and the sensing electrode and including a carbon micro-coil material, a driving unit electrically connected to the sensing electrode formed on the first surface of the substrate, configured to process the sensing information transmitted through the sensing electrode and transmit the sensing information corresponding to the variation amount of the impedance value to the control unit, and a protective layer formed surrounding the driving unit;

wherein an impedance value of the reaction layer is changed in accordance with at least any one of a change of a dielectric constant and a force caused by the contact object, and the sensing electrode transmits the sensing information with respect to the variation amount of the impedance value of the reaction layer to the driving unit.

2. The wiper driving apparatus of claim 1, wherein the reaction layer includes a resin and a dispersant.

3. The wiper driving apparatus of claim 1, wherein the reaction layer is disposed on the substrate on which the sensing electrode having a predetermined thickness is formed, and wherein a thickness of the reaction layer is thicker than a thickness of the sensing electrode.

4. The wiper driving apparatus of claim 1, wherein the sensing electrode is formed in plural number, each of the plurality of sensing electrodes includes a first electrode part disposed at an edge region of the substrate and a second electrode part extending from one end of the first electrode part in a longitudinal direction of the substrate, and an internal angle between the first electrode part and the second electrode part is an obtuse angle.

5. The wiper driving apparatus of claim 1, wherein the sensor unit comprises a via formed through the substrate, one end of the via is connected to the sensing electrode, and an other end of the via is connected to the driving unit.

6. The wiper driving apparatus of claim 1, wherein the sensor unit detects presence of rainfall and a rainfall amount based on a change of a positive imaginary part of impedance due to a force applied to the second surface of the windshield by the contact object and a change of a negative imaginary part of impedance due to a change of a dielectric constant by an object existing on the second surface.

7. The wiper driving apparatus of claim 1, comprising an adhesive member disposed between the first surface of the windshield and the sensor unit.

8. The wiper driving apparatus of claim 1, wherein the control unit determines whether the wiper is driven and sets a driving speed based on the variation amount of the impedance value.

* * * * *